United States Patent [19]

Chang et al.

[11] Patent Number: 4,706,493

[45] Date of Patent: Nov. 17, 1987

[54] SEMICONDUCTOR GAS SENSOR HAVING THERMALLY ISOLATED SITE

[75] Inventors: Shih-Chia Chang, Troy; David B. Hicks, Farmington Hills, both of Mich.

[73] Assignee: General Motors Corporation, Detroit, Mich.

[21] Appl. No.: 808,546

[22] Filed: Dec. 13, 1985

[51] Int. Cl.⁴ .............................................. G01N 27/06
[52] U.S. Cl. ...................................... 73/23; 340/634; 422/98
[58] Field of Search .................... 73/23, 27 R; 338/34, 338/35; 422/98; 340/634

[56] References Cited

U.S. PATENT DOCUMENTS

| | | | |
|---|---|---|---|
| 4,169,369 | 10/1979 | Chang | 73/23 |
| 4,224,280 | 9/1980 | Takahama et al. | 422/98 |
| 4,276,533 | 6/1981 | Tominaga et al. | 338/4 |
| 4,322,980 | 4/1982 | Suzuki et al. | 73/727 |
| 4,343,768 | 8/1982 | Kimura | 73/23 |
| 4,361,026 | 11/1982 | Muller et al. | 73/23 |
| 4,362,765 | 12/1982 | Abe et al. | 427/38 |
| 4,457,161 | 7/1984 | Iwanaga et al. | 73/23 |
| 4,580,439 | 4/1986 | Manaka | 73/23 |

OTHER PUBLICATIONS

Lahiji, G. R., et al., *A Batch-Fabricated Silicon Thermopile Infrared Detector*, in IEEE Transactions on Electron Devices, vol. ED-29, No. 1, Jan. 1982, pp. 14–22.

*Primary Examiner*—Jerry W. Myracle
*Assistant Examiner*—Joseph W. Roskos
*Attorney, Agent, or Firm*—Douglas D. Fekete

[57] ABSTRACT

A preferred semiconductor gas sensor of this invention features a gas interaction site comprising a gas sensitive semiconductor thin film and means for heating the film to an operative temperature. The thin film and heating means are carried upon a region of a substrate that is etched opposite the site to reduce the thickness of the region and thereby reduce heat flow from the region into a surrounding region.

3 Claims, 2 Drawing Figures

SEMICONDUCTOR GAS SENSOR HAVING THERMALLY ISOLATED SITE

BACKGROUND OF THE INVENTION

This invention relates to a gas sensor comprising a semiconductor thin film that is heated to an operative temperature for detecting a species in an ambient gas. More particularly, this invention relates to a semiconductor gas sensor wherein the gas sensitive thin film is heated at a thermally isolated site to minimize the effects of heating upon the remainder of the sensor.

It is known to detect a species in a composite gas using a thin film of a suitable semiconductor material whose electrical resistivity changes in response to a presence of the species. For example, a semiconductor tin oxide thin film may be used to detect nitrogen oxides $NO_x$; see U.S. Pat. No. 4,169,369 issued to Chang in 1979. The electrical resistance of the film exposed to the gas is measured and provides a basis for determining the concentration of the species. The responsiveness of the film is temperature dependent. In general, it is necessary to heat the film to a predetermined elevated temperature to optimize the sensitivity for the particular species.

The delicate thin film is carried on a substrate having a substantially greater thickness to permit convenient handling. It is proposed to mount a plurality of semiconductor thin films on a common substrate. For example, a second film may be employed to detect interference due to a species other than the primary species of interest. The films, which may have like or unlike composition, may have distinct sensing temperatures. The substrate may also include an integrated circuit for interpreting the electrical resistance measurements, the operation of which may be adversely affected by heat. In order to better control temperature at other sites of the sensor, it is desired to limit the heating of the film to the immediate location of the film. However, heating the film necessarily results in heat loss to the underlying substrate, which tends to conduct heat to other locations of the device.

It is an object of this invention to provide an improved gas sensor device comprising at least one semiconductor thin film and means for heating the film to an operative temperature, which film and heating means are located at a site on a substrate that is thermally isolated from the remainder of the device to minimize heat conduction to other sites of the device. The substrate is etched to form a thin region at the site that reduces heat flow into the substrate and thus through the substrate into surrounding regions. Thus, the film is selectively heated, independent from elements located at other sites of the sensor.

SUMMARY OF THE INVENTION

In a preferred embodiment, a gas sensor device of this invention has a thermally isolated, individually heated gas interaction site. The sensor comprises a chip-like silicon substrate, a thin region of which forms a foundation for the gas interaction site. An electrically insulative silicon dioxide coating is disposed on a first face of the substrate at the site and extends to adjacent regions of the substrate. A gas sensitive semiconductor thin film is carried on the insulative coating at the site and situated for exposure to ambient gas. An electrical resistance heating element is interposed between the substrate and the gas sensitive film. In accordance with this invention, the second face of the substrate is etched opposite the thin film and heating element to substantially reduce the substrate thickness. A preferred substrate has a thickness generally of 350 to 400 microns, but is etched at the gas interaction region to a thickness on the order of two microns.

During operation, the gas sensitive thin film is exposed to an ambient gas for detecting the presence of the species. An electrical current is applied to the heating element to selectively heat the gas sensitive film to an operative temperature. The electrical resistance of the film is measured and indicates the concentration of the species. In accordance with this invention, heat flow from the gas interaction site to the remainder of the device is reduced as a result of the thin foundation provided by the etched substrate. This not only improves the efficiency of the film heating, but thermally isolates the site from neighboring sites that may include a second gas sensitive thin film heated to different temperature or an integrated circuit element whose operation tends to be adversely affected by elevated temperature.

BRIEF DESCRIPTION OF THE DRAWINGS

This invention is better understood by reference to the following drawings.

DETAILED DESCRIPTION OF THE INVENTION

Figure 1:
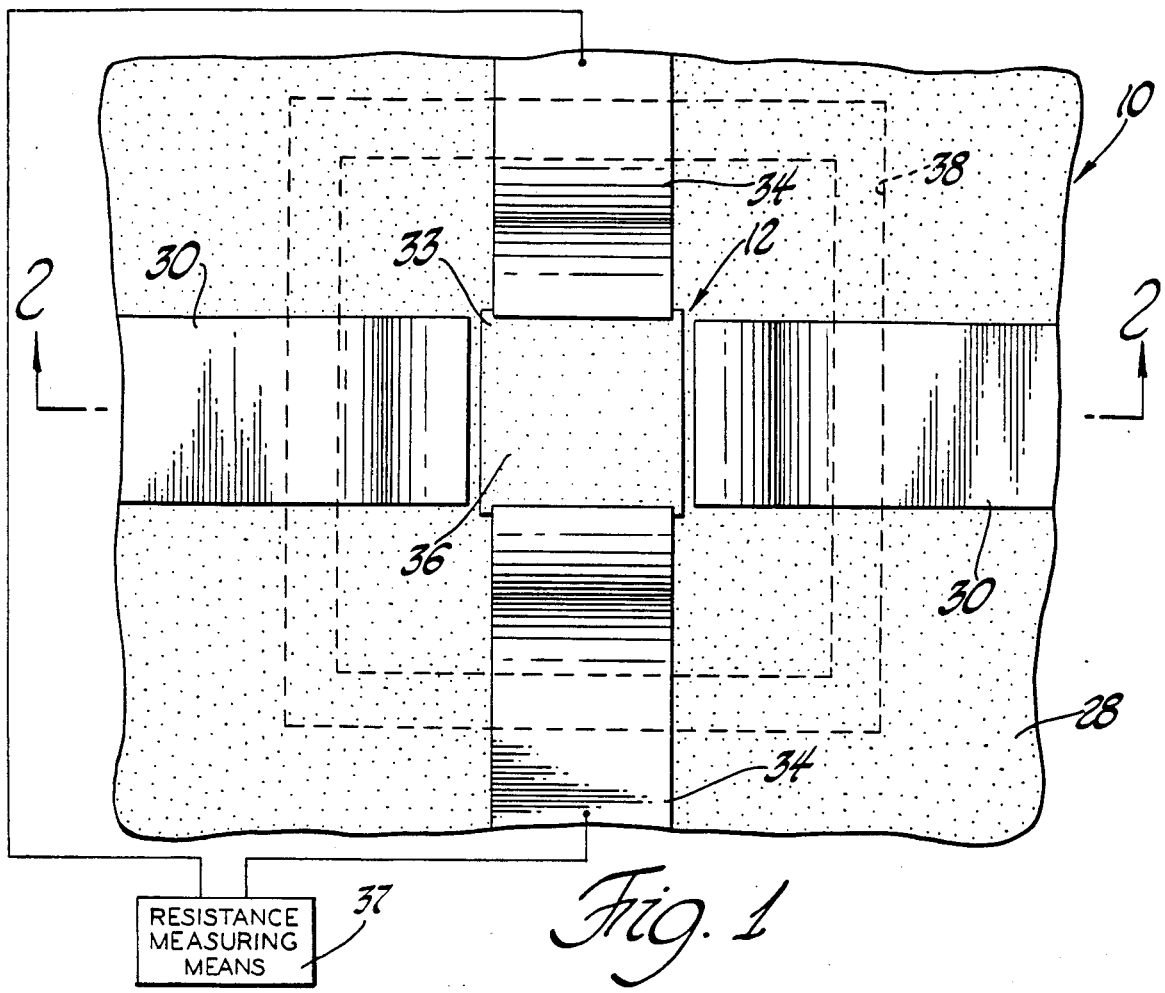
FIG. 1 is an elevational plan view of a preferred gas sensor in accordance with this invention.
Figure 2:
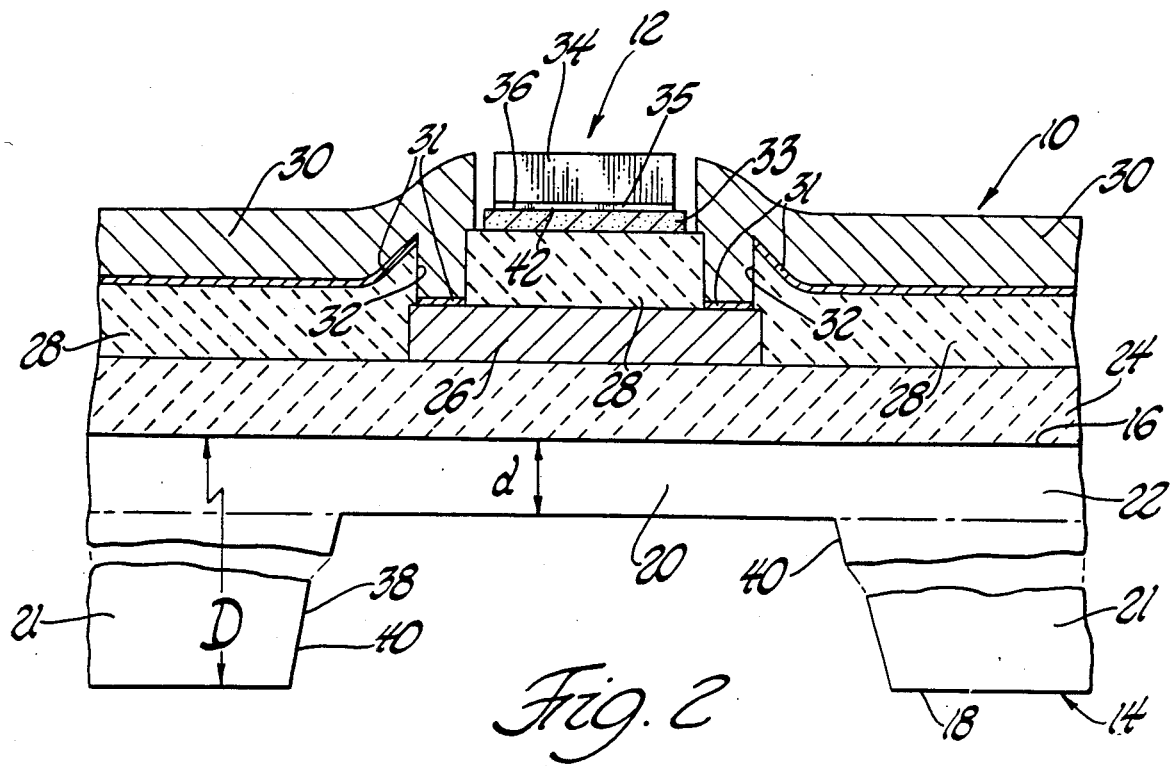
FIG. 2 is a cross-sectional view of the sensor in FIG. 1 taken along the line 2—2 looking in the direction of the arrows.

In accordance with the preferred embodiment, referring to FIGS. 1 and 2, there is depicted a portion of a gas sensor device 10 that includes a site 12 for sensing air to detect a presence of ethanol vapors. Sensor 10 may include a multiplicity of gas interaction sites similar to site 12 for detecting a plurality of constituents in the gas and also an integrated circuit for interpreting measurements made at the sites. Sensor 10 comprises a silicon chip 14 having first and second major faces 16 and 18, respectively, and including a thin region 20 having a thickness d less than two microns that forms a base for site 12 and a thick region 21 surrounding region 20 and having a thickness D of between 350 and 400 microns.

Silicon chip 14 comprises an integral boron-impregnated surface layer 22 adjacent face 16. A one-micron thick electrically insulative thermal silicon dioxide layer 24 is formed on face 16 over regions 20 and 21. A polysilicon electrical resistance heating element 26 is disposed on layer 24 over region 20. A one-micron thick electrically insulative chemical vapor deposited silicon dioxide layer 28 covers heating element 26 and layer 24. Thus, in accordance with this embodiment, silicon dioxide layers 24 and 28 cooperate to form an insulative coating extending over thin region 20 and adjacent region 21 of substrate 14.

A first pair of aluminum electrical interconnects 30 having a separately deposited chromium interface 31 contacts heating film 26 through spaced openings 32 in silicon dioxide layer 28 and extends over layer 28 from site 12 for connection to a remote electrical power source for applying an electrical current to element 26. Chromium interface 31 adjacent heating element 26 improves electrical contact reliability, particularly at elevated temperatures.

A tin oxide thin film 33 is deposited onto layer 28 overlying heating element 26 and comprises a gas contact surface 36 carrying a thin, discontinuous palladium-gold catalytic film (not shown). A second pair of aluminum electrical interconnects 34 contacts thin film 33 at opposite peripheral portions thereof and extends from site 12 for connection to a suitable motor for measuring an electrical resistance between the interconnects 34, and thus across film 33. Interconnects 34 are electrically insulated from polysilicon layer 26 by silicon dioxide layer 28 and include a separately deposited chromium interface 35 comparable to interface 31 for improved electrical contact reliability with thin film 33.

Substrate face 18 is generally planar, but includes an etched recess 38 having chamfered sides 40 that exposes boron-impregnated layer 22. Thus, film supporting region 20 of substrate 14 is formed of boron-impregnated silicon layer 22.

In a preferred embodiment, a plurality of sensors 10 are concurrently manufactured on discrete sections of a silicon wafer, which sections form chips 14, in a manner typical of integrated circuit manufacture. The thickness of the wafer is between about 350 to 400 microns, equivalent to thickness D of region 21 surrounding gas interaction region 20. Layer 22 is formed by boron ion implantation. A beam of boron ions having an acceleration voltage of about 200 KeV is projected onto face 16, and followed by a thermal diffusion step carried out at 100° C. to produce an impregnated layer 22 containing $5 \times 10^{19}$ boron atoms per cubic centimeter and having a thickness of about two microns. After boron impregnation, chip 14 is heated in the presence of oxygen to form silicon dioxide layer 24 that is approximately one micron thick. A polysilicon layer is then deposited onto silicon dioxide layer 24 by chemical vapor deposition. Element 26 is defined using photolithography and unwanted polysilicon is removed by plasma etching utilizing sulfur hexafluoride. Silicon dioxide layer 28 is formed by a reaction of silane and oxygen and deposited over layer 24 and polysilicon element 26.

A layer of semiconductor tin oxide having a thickness of about 100 nanometers is sputter deposited onto the surface of layer 28. Sputter deposition is carried out in an atmosphere composed of eight parts argon and two parts oxygen and utilizing a target formed of tin oxide. Sputter deposition of tin oxide material to form a gas sensitive film is described in U.S. Pat. No. 4,169,369, incorporated by reference. After tin oxide material is deposited, film 33 is defined by photolithography and excess tin oxide material is removed by silicon tetrachloride reactive ion etching.

A photoresist material is applied to the surface of layer 28 and film 33 and developed so as to expose layer 28 for etching openings 32. Openings 32 are formed by wet chemical etching utilizing a buffered hydrogen fluoride solution. The photoresist material is removed and a chromium flash about 500 Angstroms thick is vacuum deposited onto the surface, followed by vacuum deposition of an aluminum layer about one micron thick. Interconnects 30 and 34 are defined by photolithography. Unwanted aluminum is removed utilizing an etch solution composed of 16 parts phosphoric acid, one part nitric acid, one part acetic acid and two parts water. Unwanted chromium is removed using a commercial etching solution to re-expose layers 28 and 33. Gold and palladium are concurrently vacuum deposited onto the surface, including the exposed surface 36 of film 33, in an amount equivalent to an average film thickness of 25 Angstroms, but which does not produce a continuous, uniform film but rather forms dispersed isolated deposits.

While protecting the multi-layer structure overlying surface 16, a photoresist coating is applied to face 18 and developed to expose the substrate 14 at site 12. Substrate 14 is anisotropically etched by immersion in an aqueous EDP solution containing 35.1 mole percent ethylenediamine and 3.7 mole percent pyrocatechol. In general, the EDP solution rapidly attacks neat silicon, but only slowly attacks borondoped silicon. Thus, boron-impregnated layer 22 provides an effective etch stop.

For sensing ethanol in an air sample, the semiconductor tin oxide thin film 33 is exposed to the air sample. A predetermined electrical current of about 40 milliamperes and about three volts is passed through polysilicon heating element 26 between interconnects 30 to heat film 33 to an operative temperature of about 250° C. The resistance of film 33 is measured between interconnects 34 by connecting the interconnects to an ohmmeter or other suitable resistance measurement means 37. The resistance of film 33 decreases in response to an increased ethanol concentration in the sample. Referring to FIG. 2, gas sensitive film 33 is separated from heating element 26 by silicon dioxide layer 28 and similarly separated from substrate 14 by silicon dioxide layer 24. Thus, during operation, particularly for an extended time, region 20 is expected to be heated comparable to film 33. As a result of etched recess 38, the mass of region 20 is decreased, reducing the heat loss to substrate 14, and accordingly the electrical power required to heat film 33. In addition, heat flow from region 20 into surrounding region 21 is substantially reduced. Thus, the deleterious effects of heat on operations carried out on sensor 10 remote from site 12 are reduced. In general, the thickness of the chip is equivalent to the wafer and sufficient to permit convenient handling without breakage. Support for thin film 33 and heating element 26 at site 12 is enhanced by the coating formed by layers 24 and 28 that bridges region 20.

In the described embodiment, the semiconductor thin film is composed of tin oxide having a palladium-gold catalyst on the exposed surface. A similar sputtered tin oxide film without the catalyst may be utilized for detecting in air. In general, the semiconductor film may be formed of any suitable semiconductor material, including zinc oxide, titanium oxide, indium oxide, vanadium oxide or cobalt oxide. Optionally, the film may contain noble metal catalyst either applied discontinuously to the surface, as in the described embodiment, or dispersed in the film. Selection of a suitable film material, and optionally a catalyst, is dependent upon the gas to be analyzed and the species to be detected. Also, this invention is not limited to thin films formed by sputtering, but rather the thin film may be formed by any suitable method, depending upon the nature of the semiconductor material.

In the described embodiment, the silicon chip was etched to produce the thin region utilizing an EDP solution. Other techniques for etching silicon may be substituted, for example, wet etching using a potassium hydroxide solution.

While this invention has been described in terms of certain embodiments thereof, it is not intended that it be limited to the above description but rather only to the extent set forth in the claims that follow.

The embodiments of the invention in which an exclusive property or privilege is claimed are defined as follows:

1. A gas sensor device for detecting a species in an ambient gas and having a localized, thermally isolated gas interaction site, said device comprising
    a silicon substrate including a film support region at said gas interaction site and a region adjacent the film support region, said substrate being etchedly recessed opposite the gas interaction site such that the thickness of the film support region is substantially reduced relative to the adjacent region,
    an electrically insulative coating overlying the substrate film support region,
    a gas sensitive semiconductor thin film supported upon the insulative coating at said gas interaction site and situated for exposure to ambient gas, and
    means at the gas interaction site for selectively heating the gas sensitive thin film to a temperature operative for detecting the species, whereby heat flow from the gas interaction site through the substrate is substantially reduced as a result of the reduced thickness of the substrate film support region.

2. A gas sensor device for detecting a species in an ambient gas and having a localized, thermally isolated, independently heated qas interaction site, said device comprisinq
    a silicon substrate includinq a film support region at said gas interaction site and an adjacent region about the film support region, said substrate having a first major face whereupon is located the gas interaction site and an opposite second major face, said second face being etchedly recessed opposite the gas interaction site such that the thickness at the film support region is substantially reduced relative to the adjacent region,
    an electrically insulative silicon dioxide coating overlying the substrate first face at the film support region,
    a gas sensitive semiconductor thin film supported upon the insulative coating at said gas interaction site and situated for exposure to ambient gas, and
    electrical resistance means interposed between said substrate and said gas sensitive thin film at the gas interaction site for heating the gas sensitive thin film to a temperature operative for detecting the species, said means being electrically insulated from the gas sensitive thin film by a layer of said insulative coating, whereby heat flow from the gas interaction site to the adjacent region is substantially reduced as a result of the reduced thickness of the substrate film support region.

3. A gas sensor device for detecting a species in an ambient gas and having a localized, thermally isolated, independently heated gas interaction site, said device comprising
    a silicon substrate including a film support region at said gas interaction site and an adjacent region surrounding the film support region, said substrate having a first major face and an opposite second major face, said second face being etchedly recessed opposite the gas interaction site such that the thickness at the film support region is substantially reduced relative to the adjacent region,
    an electrically insulative silicon dioxide coating overlying the substrate first face including the film support region,
    a gas sensitive semiconductor thin film supported upon the insulative coating at said gas interaction site and situated for exposure to ambient gas,
    polysilicon heating element interposed between said substrate and said gas sensitive thin film at the gas interaction site for heating the gas sensitive thin film, said element being electrically insulated from the gas sensitive thin film by a first layer of said insulative coating and from the substrate by a second layet of said insulative coating,
    means for connecting the polysilicon element to an electrical power source for resistively heating the element to a temperature operative for detecting the species, whereupon heat loss into the substrate is reduced as a result of the reduced thickness of the substrate film support region, and
    means for connecting the thin film to a remote electrical resistance measurement means for measuring the electrical resistance of the film, which resistance provides a basis for detecting the presence of the species in the gas.

* * * * *